(12) United States Patent
Hendriks et al.

(10) Patent No.: US 8,040,495 B2
(45) Date of Patent: Oct. 18, 2011

(54) METHOD AND DEVICE FOR OPTICAL ANALYSIS OF A TISSUE

(75) Inventors: Bernardus Hendrikus Wilhelmus Hendriks, Eindhoven (NL); Antonius Theodorus Martinus Van Gogh, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 71 days.

(21) Appl. No.: 12/528,088

(22) PCT Filed: Feb. 22, 2008

(86) PCT No.: PCT/IB2008/050652
§ 371 (c)(1),
(2), (4) Date: Aug. 21, 2009

(87) PCT Pub. No.: WO2008/104913
PCT Pub. Date: Sep. 4, 2008

(65) Prior Publication Data
US 2010/0033719 A1    Feb. 11, 2010

(30) Foreign Application Priority Data
Feb. 26, 2007  (EP) ..................... 07300822

(51) Int. Cl.
*G01N 21/00*  (2006.01)

(52) U.S. Cl. ............. 356/72; 356/73; 356/337; 356/343
(58) Field of Classification Search .................. 356/317, 356/445, 326, 72–73, 337, 343; 600/476, 600/310
See application file for complete search history.

(56) References Cited

U.S. PATENT DOCUMENTS
5,760,901 A   6/1998 Hill
(Continued)

FOREIGN PATENT DOCUMENTS
WO         9810269 A1    3/1998
(Continued)

OTHER PUBLICATIONS

Elsner et al: "Imfrared Imaging of Sub-Retinal Structures in the Human Ocular Fundus"; Vision Research, Nol. 36, No. 1, pp. 191-225, 1996.

(Continued)

*Primary Examiner* — Tarifur Chowdhury
*Assistant Examiner* — Abdullahi Nur

(57) ABSTRACT

The invention relates to a method and device for analyzing a tissue (70), which comprises: —irradiating the tissue (70) with light focused on a focal region (40); —collecting light coming back from the focal region (40) into a first detection device (100A), the first detection device (100A) being arranged to only collect the light coming back from the focal region (40), on a first detection area (140A), by confocal spectroscopy, in order to generate a first signal, containing information on an optical property of the tissue (70); —collecting light, scattered from the focal region (40) to at least a second region (60), coming back from the second region (60), into a second detection device (100B), the second detection device (100B) being arranged to only collect the light coming back from the second region (60), on a second detection area (140B), in order to generate a second signal, —using the first and second signals in order to get information on the scattering and/or absorption coefficients of the tissue (70) in the region between the focal region (40) and the second region (60). Thanks to the invention, information can be gathered on the scattering and/or absorption properties of the tissue.

13 Claims, 2 Drawing Sheets

U.S. PATENT DOCUMENTS

| | | |
|---|---|---|
| 6,480,285 B1 | 11/2002 | Hill |
| 6,657,216 B1 | 12/2003 | Poris |
| 2003/0076571 A1 | 4/2003 | MacAulay et al. |
| 2005/0141082 A1 | 6/2005 | Yoshida |
| 2005/0213206 A1 | 9/2005 | Okugawa et al. |
| 2007/0057211 A1 * | 3/2007 | Bahlman et al. ............... 250/584 |

FOREIGN PATENT DOCUMENTS

| | | |
|---|---|---|
| WO | 0248688 A1 | 6/2002 |
| WO | 02077695 A1 | 10/2002 |
| WO | 02088818 A1 | 11/2002 |
| WO | 2004072695 A2 | 8/2004 |
| WO | 2005029051 A1 | 3/2005 |

OTHER PUBLICATIONS

Fang et al: "Noninvasive Sizing of Subcellular Organelles With Light Scattering Spectroscopy"; IEEE Journal of Selected Topics in Quantum Electronics, vol. 9, No. 2, pp. 267-276, Mar./Apr. 2003.

Hendriks et al: "Miniaturised High-Numerical Aperture Singlet Plastic Objective for Optical Recording"; Japanese Journal of Applied Physics, vol. 44, No. 9A, pp. 6564-6567, 2005.

"Biomedical Photonics Handbook"; Ed. By Tuan Vo-Dinh, CRC Press, 2003, Chapters 2-4.

* cited by examiner

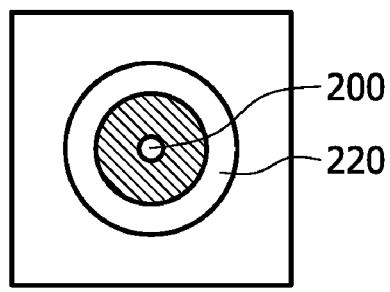
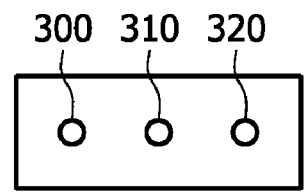
FIG. 2
FIG. 3
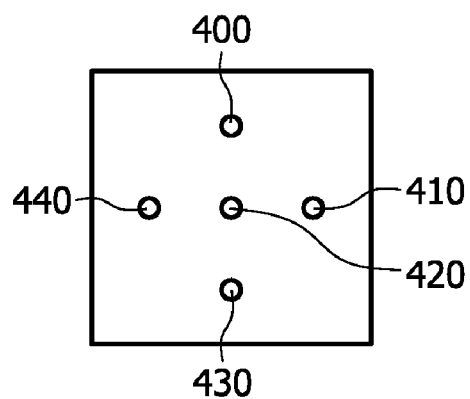
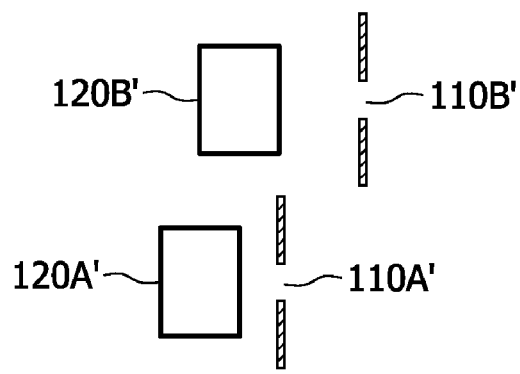
FIG. 4
FIG. 5

METHOD AND DEVICE FOR OPTICAL ANALYSIS OF A TISSUE

FIELD OF THE INVENTION

The invention relates to a method and device for optical analysis of a tissue.

BACKGROUND OF THE INVENTION

Optical measurements are performed to determine physical properties of tissues. In those measurements, light is irradiated on a tissue, interacts with the tissue and light coming back is detected and analyzed, so as to deduce therefrom properties of the tissue. Those measurements are used, for instance, for cancer diagnosis of a living tissue, by discrimination of cancerous and normal tissues.

Light coming back from the probed region of the tissue contains information useful for the analysis, related to the optical properties of the probed region of the tissue. Many techniques show that there exists a need of determining, besides this information, the scattering and/or absorption properties of the tissue nearby the probed region of the tissue. Indeed, for instance in cancer detection, changes in the scattering and/or absorption coefficients is an important signature to discriminate cancerous tissue from normal tissue.

WO 2005/029051 discloses a method and device for determining a physical feature of a medium, comprising:
  producing radiation with a light source;
  placing a probe on a sample of the medium, the probe comprising a first optical fiber having a first diameter, and at least a second optical fiber having a second diameter;
  sending light coming from the light source, through the first optical fiber;
  collecting first backscattered radiation through the first optical fiber and second backscattered radiation through the second optical fiber;
  producing a first signal based on the first backscattered radiation, and a second signal based on the second backscattered radiation;
  determining a measured differential backscatter signal as a function of wavelength using the first and second signals, characterized by
  calculating the physical feature by curve fitting the measured differential backscatter signal to a backscatter function, in which the backscatter function is a function of a mean free path of photons.

However, such a method or device implies using two fibers positioned alongside each other, which is not very practical. Furthermore, with the use of fibers, the tissue cannot be scanned, but only probed point by point, in the superficial layers such as the epithelial layer.

SUMMARY OF THE INVENTION

It is therefore an object of the present invention to provide a method and device for analyzing a tissue, which permits to get information on the scattering and/or absorption properties of the tissue around the probed regions, is of simple implementation and allows scanning the tissue.

In accordance with the present invention there is provided a method for analyzing a tissue, which comprises:
  irradiating the tissue with light focused on a focal region;
  collecting light coming back from the focal region into a first detection device, the first detection device being arranged to only collect the light coming back from the focal region, on a first detection area, by confocal spectroscopy, in order to generate a first signal, containing information on an optical property of the tissue;
  collecting light, scattered from the focal region to at least a second region, coming back from the second region, into a second detection device, the second detection device being arranged to only collect the light coming back from the second region, on a second detection area, in order to generate a second signal,
  using the first and second signals in order to get information on the scattering and/or absorption coefficients of the tissue in the region between the focal region and the second region.

Confocal spectroscopy is a technique which permits to analyze a tissue. Since light coming back from the tissue is detected on a detection area arranged to collect only light coming from the focal region, scattered light does not hamper the image quality. With the method of the invention, the information gathered in the first detection device is combined with the information gathered in the second detection device, which permits to get information on the scattering and/or absorption coefficients of the tissue around the focal region, since the light coming back from the second region has traveled between the focal region and the second region and therefore contains information on the scattering and/or absorption properties of the tissue between those regions.

Confocal spectroscopy permits to scan the tissue and obtain a 3D image of it (3D means three-dimensional). Therefore, according to an embodiment, a plurality of focal regions are irradiated in order to scan the tissue by confocal spectroscopy, so as to get information on the 3D structure of the tissue, and the information on the scattering and/or absorption coefficients is combined with the information on the 3D structure of the tissue in order to get information on the scattering and/or absorption coefficients of the tissue as a function of the 3D position in the tissue.

According to an embodiment, the focal region is a focal point and/or the second region is a second point.

According to an embodiment, light is collected from a plurality of second regions for each focal region.

According to an embodiment, the detection devices are further arranged to measure fluorescence of the tissue.

According to an embodiment, fluorescence is measured in a spatially resolved manner.

According to an embodiment, the method of the invention is applied to tissue discrimination.

According to an embodiment, the method of the invention is applied to the preceding steps of real-time in-vivo optical cancer detection.

The invention also relates to a device for analyzing a tissue, which comprises:
  means for irradiating the tissue with light focused on a focal region;
  a first detection device for collecting light coming back from the focal region, the first detection device being arranged to only collect the light coming back from the focal region, on a first detection area, by confocal spectroscopy, in order to generate a first signal, containing information on an optical property of the tissue;
  a second detection device for collecting light, scattered from the focal region to at least a second region, coming back from the second region, the second detection device being arranged to only collect the light coming back from the second region, on a second detection area, in order to generate a second signal, means for using the first and second signals in order to get information on the scattering and/or absorption coefficients of the tissue in the region between the focal region and the second region.

According to an embodiment, light is focused through a converging lens.

According to an embodiment, the detection devices each comprise at least a detector having the shape of the detection area and therefore defining alone the detection area.

According to an embodiment, the detection devices comprise pixelated detectors, comprising pixels which can be activated so as to define the detection areas.

According to an embodiment, the pixelated detectors are CCD detectors or CMOS detectors.

According to an embodiment, the first and second detection devices comprise a detector and a plate, with at least an aperture, positioned in front of the detector in order to define the detection area.

According to an embodiment, the detectors are not in the same plane.

According to an embodiment, the detection devices both comprise a detector and a common plate with at least one aperture placed in front of each detector.

According to an embodiment, the plate comprises a central pinhole, related to the focal region, and an annular aperture, related to the second region.

According to an embodiment, the plate comprises three pinholes, one pinhole related to the focal region and the two other pinholes, placed on each side symmetrically with reference to the first pinhole, related to two different positions of second regions.

According to an embodiment, the plate comprises a central pinhole, related to the focal region, surrounded by four pinholes, in a cross configuration, related to four positions of second regions.

According to an embodiment, the device is integrated into an endoscope or a catheter.

These and other aspects of the invention will be more apparent from the following description, with reference to the attached drawings.

BRIEF DESCRIPTION OF THE DRAWINGS

FIG. 2 is a schematic front view of a first particular geometry of a detection device for implementing the method of the invention;

FIG. 3 is a schematic front view of a second particular geometry of a detection device for implementing the method of the invention;

FIG. 4 is a schematic front view of a third particular geometry of a detection device for implementing the method of the invention and FIG. 5 is a schematic front view of a fourth particular geometry of a detection device for implementing the method of the invention.

DETAILED DESCRIPTION OF THE EMBODIMENTS

Figure 1:
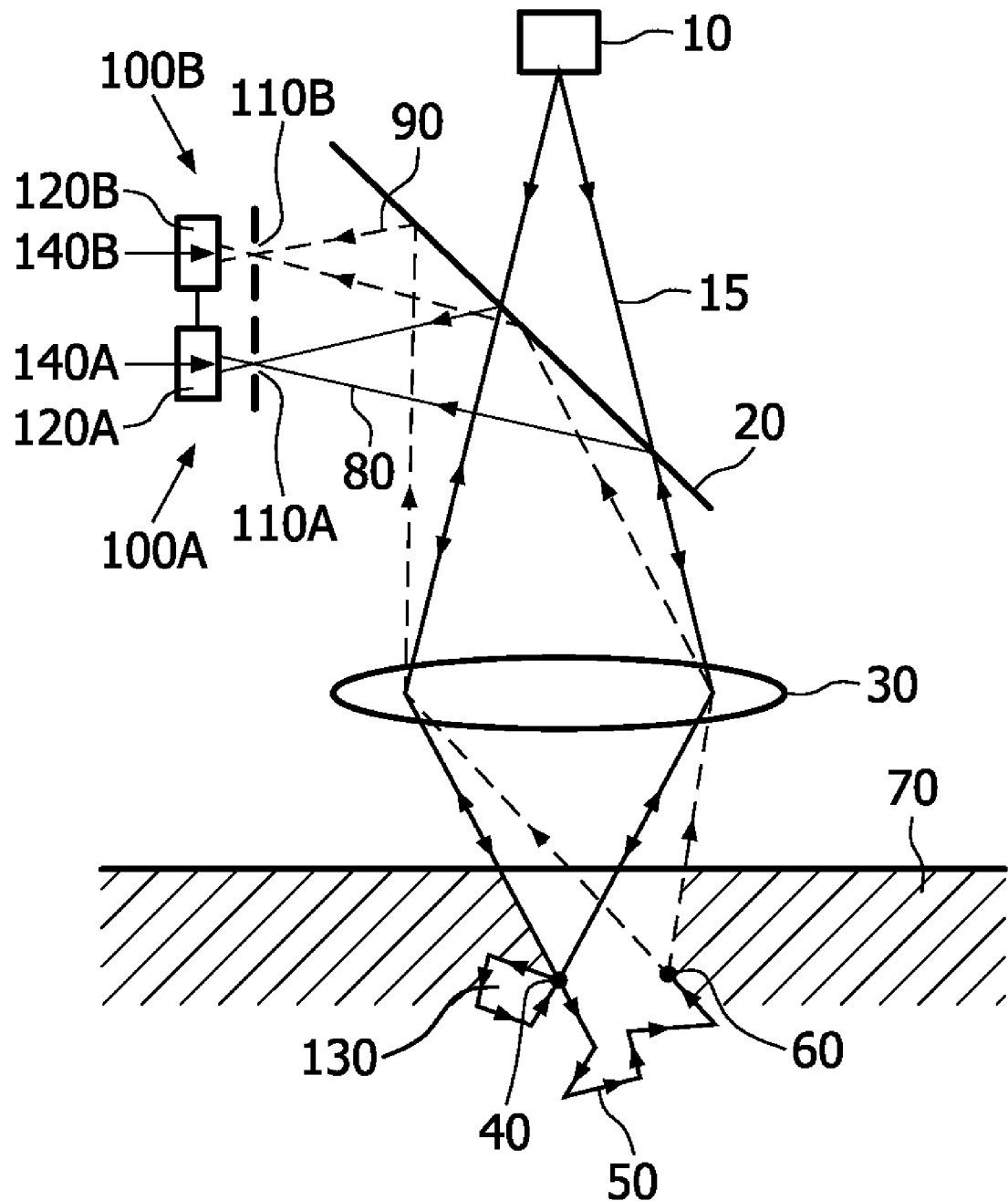
FIG. 1 is a schematic side view of a device for implementing the method of the invention.

Before describing in details the features of the invention, the principles of confocal microscopy will now be briefly presented. In confocal microscopy, a tissue is imaged by irradiating a focused spot in the tissue and detecting the reflected light by a detector with, for instance, a pinhole in front of it, appropriately positioned relative to the focused light point; due to the pinhole, light being reflected from the focal point, on which the incident light beam is focused, can reach the detector, but light being scattered around the focused spot does not reach the detector. By scanning through the tissue, a 3D image can be formed, on the basis of the reflected light detected. Light scattered through the tissue, normally hampering the image quality of a microscope image, is filtered out, leading to a good quality of the 3D image of the tissue. Since the image is formed on the basis of the light reflected from the tissue, the image only contains information related to the single backscattering or reflection coefficient of the tissue. Confocal microscopy is widely used in biology for imaging biological tissues.

In confocal microscopy, it is just the global intensity of the reflected light which is measured. Confocal spectroscopy may also be performed, where the light beam coming back can be intensity integrated, as in microscopy, but also spectrally resolved, in order to obtain the intensity of the light beam at its different wavelengths, and therefore an absorption spectrum.

The invention is an improvement of known confocal spectroscopy techniques and permits to get information on the scattering and/or absorption properties of the tissue around the focal region, thanks to the use of a second detection device that collects the light coming from a second region, at a position different from the one of the original focused spot. This different position is not directly lighted by the incident light beam but by light scattering from the focal region. Combining the signals generated by reflection from the focal region and scattering from the focal region to the second region permits to get information on the scattering and/or absorption properties of the tissue between the focal region and the second region. According to an embodiment, by scanning the tissue, it is possible to determine changes in the scattering and/or absorption coefficients of the tissue as a function of the 3D position in the tissue.

It has to be noticed that, when light travels from the focal region to a second region, the light coming back from the second region contains information on both the scattering and the absorption coefficients. Information can therefore be gathered on both the scattering coefficient and the absorption coefficient. However, one can choose to only get information on the scattering coefficient or on the absorption coefficient and this is why the invention is presented in relation with getting information on the "scattering and/or absorption coefficients".

In most of the embodiments described below, reference will be made to the scattering coefficient, because the invention is presented in relation with getting information on the scattering coefficient. However, it should be understood that the same methods and devices according to the invention can be used for determining information on the absorption coefficient or for determining information on both the scattering and absorption coefficients. Indeed, both the scattering coefficient and the absorption coefficient are useful information for tissue analysis.

With reference to FIG. 1, a device for implementing the optical analysis method of the invention, for the analysis of a tissue 70, comprises a light source 10, a partial beam splitter 20, an objective lens 30, which is a converging lens 30, a first detection device 100A, comprising a plate with an aperture 110A and a detector 120A, the aperture 110A being in front of the detector 120A, and a second detection device 100B, comprising a plate with an aperture 110B and a detector 120B, the aperture 110B being in front of the detector 120B. In the embodiment described, the apertures 110A, 110B are pinholes 110A, 110B.

The light source 10 emits a light beam 15 which may be, for instance, a broadband or single-wavelength light beam 15. This incident light beam 15 passes through the beam splitter 20 towards the objective lens 30. The objective lens 30 focuses the light into a spot 40 in the tissue 70; this spot will be referred to as the focal point 40. A focal point is a point or region wherein the light of a light beam is concentrated. The light focus into a focal point is herein obtained by means of a converging lens 30, but it could be obtained by any suitable means such as, for instance, a lens made out of a grating.

The light beam 80 coming back from the focal point 40 is imaged back by the objective lens 30 and reflected by the partial beam splitter 20 in the direction of the first detection device 100A. It should be noticed that this light beam 80 comprises light directly reflected back or single backscattered from the focal point 40 of the tissue 70, but also light multiple scattered and reaching the focal point 40 again, as illustrated by the light path 130 on FIG. 1. However, the signal related to multiple scattering (130) is very weak compared to the signal related to reflection and single backscattering.

The light beam 80 coming back from the focal point 40 passes through the first pinhole 110A and reaches the first detector 120A on a first detection area 140A. The first detector 120A may be of any kind, suitable to detect a light beam and connected to means which can generate therefrom a first signal (an electric signal), representing the features of the light beam. In other words, the first detector 120A is adapted to spectroscopy measurements. The signal may for instance be intensity integrated or spectrally resolved.

The first pinhole 110A assures that only light coming back from the focal point 40 can reach the detector 120A, on the detection area 140A. In other words, the first pinhole 110A is configured and disposed, relatively to the detector 120A, the tissue 70, the objective lens 30 and the beamsplitter 20, so that the light passing through can only be originated from the focal point 40.

Therefore, the device for implementing the method of the invention permits to have a first detection path, going from the light source 10 to the focal point 40, via the beamsplitter 20 and the lens 30, and then from the focal point 40 to the first detection 140A, via the lens 30, the beamsplitter 20 and through the pinhole 110A.

Apart from this first detection path, a second detection path is provided.

Light is scattered from the focal point 40 into the tissue 70, and notably towards a second point referenced 60 on FIG. 1. This scattered light for instance follows the light path referenced 50 on FIG. 1. The light may be scattered only a few times from the focal point 40 to the second point 60, but it is mainly multiple scattered.

The light beam 90 coming from the second point is imaged back by the objective lens 30 towards the partial beam splitter 20, where it is reflected in the direction of the second detection device 100B. This light beam 90 passes through the second pinhole 110B towards the second detector 120B, on the second detection area 140B.

Again, the second detector 120B is adapted to detect the intensity of the light beam and connected to means adapted to generate a second signal representative of the features of the light beam. This signal may for instance be intensity integrated or spectrally resolved.

The second pinhole 110B assures that only light coming back from the second point 60 can reach the second detector 120B, on the detection area 140B. In other words, the second pinhole 110B is configured and disposed, relatively to the detector 120B, the tissue 70, the objective lens 30 and the beamsplitter 20, so that the light passing through can only be originated from the second point 60.

The signal from the second detector 120B contains information on the scattering properties of the tissue 70 rather than on the reflection coefficient.

As alluded to above, the first and second detectors 120A, 120B may measure the total intensity or the spectrally resolved signal.

By combining and/or comparing the first and second signals, respectively generated by the first and second detectors 120A, 120B, information on the scattering properties of the tissue 70 between the focal point 40 and the second point 60 can be obtained. The device for implementing the method of the invention comprises means adapted to obtain this information on the scattering properties; those means will not be described in many details, since they are accessible to the person skilled in the art; only exemplary methods will briefly be discussed below. The corresponding means may comprise computer programs.

According to an embodiment, a usual method may be implemented, where the two signals are compared, the difference between both being namely linked to scattering. By adequate calibration and calculations, the information looked for is calculated. Such methods are described in Biomedical Photonics Handbook, Editor-in-Chief Tuan Vo-Dinh, CRC Press LLC, Florida ISBN 0-8493-1116-0, part I: Photonics and Tissue Optics, especially in chapters 2-4. A method is also described in WO 2005/029051, already cited above.

According to an embodiment, the focused spot can be made linearly polarized and the signals detected through both pinholes 110A, 110B can be polarization resolved and spectrally resolved.

From information on the polarization changes due to scattering, the person skilled in the art may deduce information on the biological structure of the tissue such as, for instance, information on the shape of the nuclei of the cells (whether they are regular or irregularly shaped), etc. Those are information which are in addition to the information gathered thanks to the method of the invention.

According to a particular embodiment, a polarized light beam 15 is irradiated on the tissue 70 and polarization detection is performed, by placing a polarizer in front of the second detector 120B. This permits to discriminate between photons being scattered only a few times and photons being scattered multiple times. Indeed, photons being multiple scattered become depolarized; hence, if the polarizer in front of the second detector 120B selects only light having the same polarization as the incident light beam 15, only photons that are only a few times scattered are measured, their polarization being kept unchanged. In this way, information on the local scattering properties of the medium near the focal point 40 is obtained.

Any other suitable method, accessible to the person skilled in the art, may be implemented in order to get information on the scattering properties of the tissue 70.

Optionally, for one focal point 40, a plurality of different second points 60 in the vicinity of the focal point 40 may be scanned, by changing the arrangement and position of the second detection device 100B, since to each position of the second pinhole 110B and detector 120B corresponds a unique position of a second point 60. Particular embodiments will be discussed in more details below.

According to an embodiment of the invention, the tissue 70 may be scanned in 3D by pointing the focused spot 40 at different 3D locations in the tissue 70. Therefore, a 3D image of the tissue 70 is obtained with the information gathered from the first detection device 100A, in a conventional confocal spectroscopy manner, while information is collected, for each position of the focal point 40, on the scattering properties around that focal point 40, thanks to the second detection device 100B. The signal from the first detection device 100A may therefore be combined, for each position of the focused spot 40, with the signal from the second detection device 100B; therefrom, the scattering coefficient may be calculated for each 3D position of the focused spot 40. Thanks to the method and device of the invention, the scattering coefficient of the tissue 70 may therefore be calculated as a function of the 3D position in the tissue 70. This information is obtained for any depth and not only for the superficial layers.

As explained above, information on the scattering coefficient as well as information on the absorption coefficient may be obtained. Indeed, the amount of light reaching the second point 60 depends on the absorption coefficient of the tissue 70. As a result the second signal depends strongly on the scattering and absorption properties of the tissue in the region around the focused spot 40.

Obtaining information on the scattering coefficient as a function of the 3D position is valuable for evaluation of the tissue properties. For instance in the case of tissue discrimination, and in particular cancer detection, the tissue properties change as a function of depth. Before the morphology of the tissue changes, changes in protein content and DNA of the tissue will occur that affect the scattering coefficient as a function of depth. Being able to detect these changes, cancer detection can be done in an early stage and also the extensiveness of the cancer can be determined.

As far as the cancer detection application is concerned, information from conventional confocal spectroscopy (i.e. the signal from the first detection device 100A) permits to detect regions susceptible of being abnormal; thanks to the invention, other information (e.g. scattering properties as a function of the 3D position) can be gathered on those regions, which permits to corroborate the suspicion of abnormality; indeed, the scattering properties are an important signature for the tissue, which permit to discriminate abnormal tissue from normal tissue.

The method of the invention can be used for the preliminary steps of non-invasive real-time in-vivo cancer detection.

To implement the method of the invention, no fibers are used, while no instruments are in contact with the tissue 70. The method and device of the invention are therefore very simple to implement.

According to a particular embodiment of the invention, by using a single-wavelength incident beam and low-pass filters in the detection paths, the detection devices 100A, 100B can be used to measure fluorescence in a spatially resolved manner, that is to say, fluorescence is measured as a function of the 3D position in the tissue. This gives additional information on the local absorption, scattering properties and hence on the biological properties of the tissue.

In such a case, the device of the invention may comprise a low-pass filter in front of each detector 120A, 120B or the beam splitter 20 may be replaced with a dichroic mirror. The first detector 120A measures the intrinsic tissue fluorescence originating from the focal point 40. This signal gives information on the biomolecular nature of the tissue at the focal point 40. The second detector 120B measures the intrinsic tissue fluorescence originating from the second point 60. The signal from the second detector 120B is lower than that from the first detector 120A and the signal attenuation of the signal depends on the scattering and absorption properties of the tissue. Hence the magnitude of the signal detected by the second detector 120B yields information on the scattering and absorption properties along the photon paths from the focal point 40 to the second point 60 as well, whereas the shape of the fluorescence spectrum gives information on the biomolecular state nature at the second point 60.

By using only one low-pass filter in front of one of the detectors 120A, 120B, additional information on the tissue 70 under study can be obtained.

In any of the embodiments presented above, by choosing an objective 30 with a higher numerical aperture, the intensity at the focal point 40 can be increased. This improves the signal intensity from both the focal point 40 and the second point 60. This is especially important in the fluorescence embodiment presented above. In this latter case, the light source 10 should preferably be a laser. Of course, a laser may also be used for the other embodiments of the invention.

Various geometries of the pinholes can be contemplated, therefore changing accordingly the position of the second point or points 60. Indeed, and as already announced above, light coming back from a plurality of second points 60 or even a continuous second region can be detected thanks to the second detection device 100B with an adapted geometry. The first detection device 100A will usually comprise a single aperture, in order to detect light from a focal point 40 as tiny as possible. Four particular embodiments of the detection devices 100A, 100B will now be described. In those embodiments, the detection devices comprise a common plate with at least one aperture placed in front of each detector. Only the geometry of the apertures will be described.

With reference to FIG. 2, the detection device comprises a central pinhole 200, related to the focal point 40, and an annular aperture 220, related to the second points, which in that case are a continuous circular region around the focal point 40.

With reference to FIG. 3, the detection device comprises three pinholes: one pinhole 310 is related to the focused spot 40 and the two other pinholes 300, 320, placed on each side symmetrically with reference to the first pinhole 310, are related to two different positions of second points 60. This allows determination of asymmetries in the scattering properties on one side and the other side of the focal point 40. This can be generalized to even more pinholes as shown in FIG. 4, where a central pinhole 420, related to the focused spot 40, is surrounded by four pinholes 400, 410, 430, 440 in a cross configuration, related to four positions of second points 60.

By choosing a pinhole geometry with more than five pinholes next to each other (or in a cross configuration as in FIG. 4), one can measure the absorption coefficient and the scattering coefficient quantitatively and locally by comparing the signal magnitudes originating from the various pinholes. Information on the scattering coefficient may therefore be obtained as a function of the direction from the focal point.

In FIG. 5, an embodiment is shown where the detectors 120A', 120B', similar to the ones of FIG. 1, are not in the same plane. The pinholes 110A', 110B' are not in the same plane neither. Hence in this case the device of the invention measures the scattering properties in the z-direction in the medium 70.

It should be noticed that a way to discriminate between single and multiple backscattered photons is to make use of the position and the size of the pinholes. The pinholes may play the same role as the size of the fibers in the method of WO 2005/029051. The same principle used in the method presented in this document can be used in the method of the invention, extended through out the tissue.

Various other detection geometries can be envisioned without departing from the scope of the invention. What is important is that two distinct detection areas 140A, 140B are provided. This can be obtained with plates with apertures placed in front of detectors, but other embodiments may be contemplated. As far as the apertures are concerned, it should be noticed that many types of apertures may be contemplated, such as pinholes or slits, for instance. Arrays can also be used.

According to an embodiment, only detectors can be used, without any plates with apertures, the detectors having the shape of the desired detection area and therefore defining alone the detection area. In other words, the combination of a detector and a plate with an aperture in front of it is replaced by a single detector, the shape of which is arranged to only present the desired detection area.

According to another embodiment, pixelated detectors are used. A pixelated detector is a detector comprising pixels on its detecting surface; a pixelated detector can, for instance, be a CCD detector or a CMOS detector. Pixelated detectors are known by the person skilled in the art and need not be described in details.

Since those detectors are pixelated, by only activating particular pixels of the pixelated detector, detection areas are defined on the surface of the pixelated detector, all the surface around the detection area not being sensitive to light since the pixels are not activated. The detection areas for the focal point 40 and the second points 60 may be defined on a single pixelated detector.

The detection configuration of such a detection device is simply changed by changing the activated pixels. Therefore, the use of a pixelated detector gives a lot of freedom, which is especially interesting when the tissue should be scanned.

According to another embodiment, fibers may be used, with a certain diameter corresponding to pinholes.

According to another embodiment, a miniaturized confocal setup is used, based on an aspherical objective lens. In this case the objective 30 of FIG. 1 is replaced by a single aspherical lens similar to the ones used in optical recording. This allows miniaturization of the setup to a few millimeters (see for instance: B. H. W. Hendriks, M. A. J. van As and A. A. M. van Alem, Miniaturised high-NA singlet plastic objective for optical recording, Jap. J. Appl. Phys. 44 (2005) 6554-6567). As a result of this miniaturization, the method of the invention may be implemented on the tip of a catheter or in an endoscope, for endoscopic use. This allows investigation of internal organs and tissue in the human body.

According to another embodiment, polarization filters are placed in front of the detector, in order to allow the measuring of the depolarisation of the signal as a function of scattering properties of the tissue.

Besides the magnitude of the signal at various wavelengths, also the angular distribution of the signal contains information on the optical properties of the tissue (see Fang et al., IEEE J. Sel. Topics Quant. Elec. 9 (2003), 267-276). In the above embodiments, information on the angular distribution of the signal can be obtained by moving a pinhole (or another device providing a detection area) through light beam coming back from the focused spot or the second region. In this case, a less divergent excitation beam 15 should be chosen, for a better definition of the incident angle.

In the whole description, allusion has been made to the focal point and the second point, but the term "point" should be understood as designating a point, a region or a volume. In particular, the focal point may indeed be a precise point, scattered light being measured in a second region around the focal point.

It should be understood that, depending on how precise information is required on a tissue, the person skilled in the art will choose one of the embodiments of the invention. The more information is gathered the more precise a tissue characterization can be done.

For instance, if the signals generated at the first and second detectors are the intensity of the focal and second points, information will be gathered on the averaged scattering coefficient of the tissue between those points. If the spectrum is calculated from the signals, the scattering coefficient can be resolved as a function of the wavelength. If light from several second points is measured, changes of the scattering coefficient around the focal point can be determined as a function of the direction around the first focal point. If polarization information is gathered, information on the biological structure of the tissue (such as the shape of the particles around the focal point) can be obtained. If all those information are combined and the inverse scattering problem is resolved (for instance thanks to Monte Carlo calculations, accessible to the person skilled in the art), it is even possible to reconstruct the tissue around the focal point.

The chosen embodiment will depend on what should be analyzed. For instance, if one wants to know whether a tissue is cancerous, one does not need a full reconstruction of the tissue, since knowing that the overall scattering coefficient is significantly different from normal tissue may be enough. If one wants to make a more reliable diagnosis, one may look for more information.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of analyzing a tissue, the method comprising acts of:

irradiating the tissue with initial light focused on a focal region;

collecting first light coming back from the focal region into a first detection device arranged to only collect the first light coming back from the focal region, on a first detection area by confocal spectroscopy to generate a first signal including information on an optical property of the tissue;

collecting second light scattered from the focal region to at least a second region, coming back from the second region into a second detection device arranged to only collect the second light coming back from the second region on a second detection area to generate a second signal; and using the first and second signals to get information on the scattering and/or absorption coefficients of the tissue in the region between the focal region and the second region.

2. The method according to claim 1, wherein a plurality of focal regions are irradiated in order to scan the tissue by confocal spectroscopy, so as to get information on the 3D structure of the tissue, and the information on the scattering and/or absorption coefficients is combined with the information on the 3D structure of the tissue in order to get information on the scattering and/or absorption coefficients of the tissue as a function of the 3D position in the tissue.

3. The method according to claim 2, wherein the second light is collected from a plurality of second regions for each focal region.

4. The method according to claim 1, wherein the detection devices further measure fluorescence of the tissue.

5. A device for analyzing a tissue, the device comprising:
a device for irradiating the tissue with initial light focused on a focal region;
a first detection device for collecting first light coming back from the focal region, the first detection device being arranged to only collect the first light coming back from the focal region on a first detection area by confocal spectroscopy in order to generate a first signal, containing information on an optical property of the tissue;
a second detection device for collecting second light scattered from the focal region to at least a second region coming back from the second region, the second detection device being arranged to only collect the second light coming back from the second region on a second detection area in order to generate a second signal; and
a comparator for using the first and second signals in order to get information on the scattering and/or absorption coefficients of the tissue in the region between the focal region and the second region.

6. The device according to claim 5, wherein the detection devices each comprise at least a detector having the shape of the detection area and therefore defining alone the detection area.

7. The device according to claim 5, wherein the detection devices comprise pixelated detectors, comprising pixels which can be activated so as to define the detection areas.

8. The device according to claim 5, wherein the first and second detection devices comprise a detector and a plate, with at least an aperture positioned in front of the detector in order to define the detection area.

9. The device according to claim 8, wherein the detectors are not in the same plane.

10. The device according to claim 5, wherein the detection devices both comprise a detector and a common plate with at least one aperture placed in front of each detector.

11. The device according to claim 10, wherein the plate comprises a central pinhole related to the focal region and an annular aperture related to the second region.

12. The device according to claim 10, wherein the plate comprises three pinholes, one pinhole related to the focal region and the two other pinholes placed on each side symmetrically with reference to the first pinhole related to two different positions of second regions.

13. The device according to claim 5, wherein the device is a catheter or endoscope.

* * * * *